US009339317B2

(12) United States Patent
Vogt et al.

(10) Patent No.: US 9,339,317 B2
(45) Date of Patent: May 17, 2016

(54) MIXING DEVICE FOR PREPACK VACUUM CEMENTING SYSTEM, VACUUM CEMENTING SYSTEM, AND METHOD

(75) Inventors: Sebastian Vogt, Erfurt (DE); Hubert Buechner, Nuremberg (DE)

(73) Assignee: Heraeus Medical GmbH, Wehrheim (DE)

( * ) Notice: Subject to any disclaimer, the term of this patent is extended or adjusted under 35 U.S.C. 154(b) by 381 days.

(21) Appl. No.: 13/822,546

(22) PCT Filed: Aug. 10, 2011

(86) PCT No.: PCT/EP2011/003992
§ 371 (c)(1),
(2), (4) Date: Mar. 12, 2013

(87) PCT Pub. No.: WO2012/038002
PCT Pub. Date: Mar. 29, 2012

(65) Prior Publication Data
US 2013/0182528 A1 Jul. 18, 2013

(30) Foreign Application Priority Data
Sep. 22, 2010 (DE) .......................... 10 2010 046 055

(51) Int. Cl.
*B01F 13/06* (2006.01)
*A61B 17/88* (2006.01)
(Continued)

(52) U.S. Cl.
CPC ............ *A61B 17/88* (2013.01); *A61B 17/8822* (2013.01); *A61B 17/8827* (2013.01);
(Continued)

(58) Field of Classification Search
CPC ....................................................... B29B 7/10
USPC .................................................. 366/139, 189
See application file for complete search history.

(56) References Cited

U.S. PATENT DOCUMENTS 34,299 A * 2/1862 Griffing ........................ 220/253
1,157,537 A * 10/1915 Hess ............................. 222/511
(Continued)

FOREIGN PATENT DOCUMENTS

DE 28 25 230 12/1979
DE 36 40 279 A1 6/1987
(Continued)

OTHER PUBLICATIONS

Breusch, S. J. et al.; "Der Stand der Zementiertechnik bei Hueft-totalendoprothesen in Germany;" 1999; pp. 101-107; vol. 137; Z. Orthop.; Heidelberg, Germany.
(Continued)

*Primary Examiner* — David Sorkin
(74) *Attorney, Agent, or Firm* — Norris McLaughlin & Marcus, P.A.

(57) ABSTRACT

A mixing device, for a mixable material, has at least one cartridge and a closure piece. The cartridge contains a first component of the mixable material and has a cartridge head in which at least one air opening is arranged, and the closure piece is arranged on the cartridge head in such a way that the at least one air opening in the cartridge head can be closed and opened by the closure piece. The closure piece is mounted so as to be rotatable or slideable relative to the cartridge head, and a connection extends through the cartridge head or a cartridge wall into the interior of the cartridge and connects the interior of the cartridge to a container for a second component of the mixable material.

20 Claims, 7 Drawing Sheets

Figure 1:
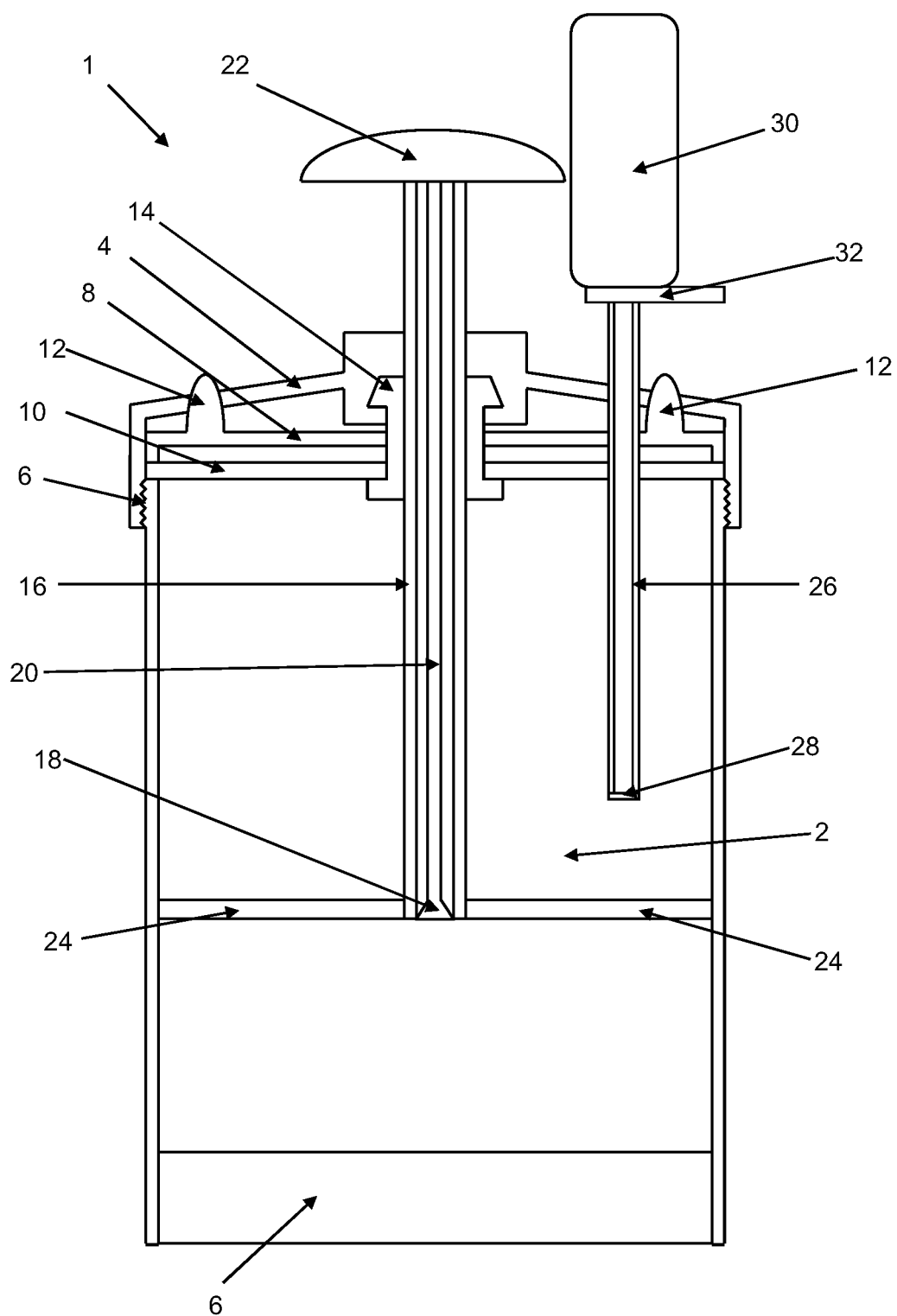

(51) Int. Cl.
  *B01F 7/00* (2006.01)
  *B01F 13/00* (2006.01)
  *B01F 15/00* (2006.01)
  *B01F 15/02* (2006.01)
  *B29B 7/10* (2006.01)
  *B01F 7/16* (2006.01)

(52) U.S. Cl.
  CPC ............. *B01F 7/007* (2013.01); *B01F 7/00716* (2013.01); *B01F 13/0018* (2013.01); *B01F 15/00071* (2013.01); *B01F 15/00798* (2013.01); *B01F 15/00974* (2013.01); *B01F 15/0278* (2013.01); *B29B 7/10* (2013.01); *B01F 7/16* (2013.01); *B01F 15/00506* (2013.01)

(56) References Cited

U.S. PATENT DOCUMENTS

| | | | | |
|---|---|---|---|---|
| 1,162,791 | A | * | 12/1915 | Lubas ............................ 220/253 |
| 1,193,954 | A | * | 8/1916 | Walden ......................... 366/343 |
| 3,140,078 | A | | 7/1964 | Krahe et al. |
| 4,671,263 | A | | 6/1987 | Draenert |
| 4,758,096 | A | | 7/1988 | Gunnarsson |
| 4,973,168 | A | | 11/1990 | Chan |
| 5,100,241 | A | | 3/1992 | Chan |
| 5,344,232 | A | | 9/1994 | Nelson et al. |
| 5,586,821 | A | | 12/1996 | Bonitati et al. |
| 5,624,184 | A | | 4/1997 | Chan |
| 5,997,544 | A | | 12/1999 | Nies et al. |
| 6,709,149 | B1 | | 3/2004 | Tepic |
| 2004/0079755 | A1 | * | 4/2004 | Graus ........................... 220/253 |
| 2004/0196735 | A1 | | 10/2004 | Barker et al. |
| 2005/0155901 | A1 | | 7/2005 | Krueger et al. |

FOREIGN PATENT DOCUMENTS

| | | |
|---|---|---|
| DE | 195 32 015 A1 | 3/1997 |
| DE | 10 2007 061 696 B4 | 3/2010 |
| DE | 10 2009 031 178 B3 | 9/2010 |
| EP | 0 692 229 A1 | 1/1996 |
| EP | 1 005 901 A2 | 6/2000 |
| EP | 1 016 452 A2 | 7/2000 |
| EP | 1 020 167 A2 | 7/2000 |
| EP | 1 031 333 A1 | 8/2000 |
| JP | S55133921 A | 10/1980 |
| JP | H08-171192 | 7/1996 |
| JP | 201002108 A | 1/2001 |
| JP | 2005096862 A | 4/2005 |
| WO | WO 94/26403 A1 | 11/1994 |
| WO | WO 97/18031 A1 | 5/1997 |
| WO | WO 99/67015 A1 | 12/1999 |

OTHER PUBLICATIONS

Charnley, John; "Anchorage of the Femoral Head Prothesis to the Shaft of the Femur"; The Journal of Bone and Joint Surgery; Feb. 1960; pp. 28-30; Manchester, England.

International Search Report, Application No. PCT/EP2011/003992, date of mailing Jan. 23, 2012.

Canadian Office Action for corresponding Canadian Patent Application No. 2,810,469 dated Dec. 1, 2014.

Chinese Office Action for corresponding Chinese Patent Application No. 201180045463.4 dated Oct. 10, 2014.

English-language translation of Japanese Office Action for corresponding Japanese Patent Application No. 2013-528530 dated Feb. 3, 2015.

Japanese Office Action for corresponding Japanese Patent Application No. 2013-528530 dated Apr. 1, 2014.

* cited by examiner

MIXING DEVICE FOR PREPACK VACUUM CEMENTING SYSTEM, VACUUM CEMENTING SYSTEM, AND METHOD

This is a 371 of PCT/EP2011/003992 filed 10 Aug. 2011 (international filing date), and claims the priority of German Application No. 10 2010 046 055.9 filed 22 Sep. 2010.

The invention relates to a mixing device for mixing a mixable material, in particular a medical cement, comprising at least one cartridge and one closure, whereby the at least one cartridge contains a first component of the mixable material and comprises a cartridge head, in which at least one ventilation opening is arranged and the closure is arranged at the cartridge head in such manner that the at least one ventilation opening in the cartridge head can be closed and opened by means of the closure.

The invention also relates to vacuum cementing system having a mixing device of this type and a method for use of a mixing device of this type or of a vacuum cementing system of this type.

In this context, the invention provides a device for mixing a cement from a monomer and a cement powder.

Polymethylmethacrylate bone cements (PMMA bone cements) have been known for decades and are based on the ground-breaking work of Sir Charnley (Charnley, J.: Anchorage of the femoral head prosthesis of the shaft of the femur. J. Bone Joint Surg. 42 (1960) 28-30.). The basic structure of PMMA bone cements has remained the same ever since. PMMA bone cements usually consist of a liquid monomer component and a powder component. The monomer component generally contains the monomer, methylmethacrylate, and an activator (N,N-dimethyl-p-toluidine) dissolved therein. The powder component consists of one or more polymers that are made by polymerisation, preferably suspension polymerisation, based on methylmethacrylate and co-monomers, such as styrene, methylacrylate or similar monomers, a radio-opaquer, and the initiator, dibenzoylperoxide. Mixing the powder component and the monomer component, a dough that can be shaped plastically is generated by swelling of the polymers of the powder component in the methylmethacrylate. Mixing the powder component and the monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

PMMA bone cements can be mixed by mixing the cement powder and the monomer liquid in suitable mixing beakers with the aid of spatulas. This procedure is disadvantageous in that air inclusions may be present in the cement dough thus formed and cause destabilisation of the bone cement later on. For this reason, it is preferred to mix bone cement powder and monomer liquid in vacuum mixing systems, since mixing in a vacuum removes air inclusions from the cement dough to a large extent and thus achieves optimal cement quality (Breusch S J et al.: Der Stand der Zementiertechnik in Deutschland. Z Orthop. 1999, 137: 101-07). Bone cements mixed in a vacuum have clearly reduced porosity and thus show improved mechanical properties. Numerous vacuum cementing systems are known and are described, for example, in the following patent documents: U.S. Pat. No. 5,624,184, U.S. Pat. No. 4,671,263, U.S. Pat. No. 4,973,168, U.S. Pat. No. 5,100,241, WO 99/67015 A1, EP 1 020 167 A2, U.S. Pat. No. 5,586,821, EP 1 016 452 A2, DE 36 40 279 A1, WO 94/26403 A1, EP 0 692 229 A1, EP 1 005 901 A2, U.S. Pat. No. 5,344,232.

Vacuum cementing systems are used in the mixing of the PMMA bone cement in a vacuum in order to remove air inclusions from the cement dough. They are designed to produce a cement dough that is as homogeneous as possible and largely free of bubbles.

Cementing systems are a refinement, in which both the cement powder and the monomer liquid are already packaged in separate compartments of the mixing systems and are mixed with each other only right before application of the cement in the cementing system (U.S. Pat. No. 5,997,544, EP 0 692 229 A1, U.S. Pat. No. 6,709,149 B1). The issues of said systems include the transfer of the monomer liquid into the cement powder and the complete mixing of said two components in order to obtain a homogeneous cement dough that contains, in particular, no clusters of cement powder that has not been wetted by the monomer liquid. In the full-prepack mixing system, Optipac™ (Biomet Switzerland), which is currently commercially available in Europe, simple tubes, which are attached on the side in the lower part of the cartridge and puncture through the cartridge wall, are used to aspirate the monomer liquid approximately from aluminium composite pouches into the centre of the cement powder through the action of a vacuum. Aluminium composite pouches are manually moved against the tubes in order to open them, whereby the tubes puncture through the wall of the pouches.

Aluminium composite pouches have been known for packaging and storing monomer liquid for only a few years. Very good experience regarding the storage properties of monomer liquid has been made with glass ampoules. Glass ampoules have been in use for decades with good success with conventional polymethylmethacrylate bone cements. Another advantage of glass ampoules, aside from perfect sealing, is that they can be produced in large numbers at low prices. It is therefore reasonable to use glass ampoules for packaging and storage of monomer liquid in prepack vacuum cementing systems.

Using cartridge systems for sterile pasty medical products, there is a need for not only the pastes, but obviously the cartridges and secondary packaging means also to be provided in sterile form to the user. For example after aseptic filling of the previously sterilised cartridges, these may be transferred directly to sterile packaging means. Moreover, it may make sense for certain products to sterilise the surfaces of filled cartridges jointly with the packaging means after packaging is completed. Aside from gamma sterilisation, which cannot be used with paste systems that can be polymerised, there is the option to use ethylene oxide gas for sterilisation.

DE 195 32 015 A1 describes a device for mixing and dispensing multi-component products. A support socket about which an ampoule holder can move in rotary manner is provided on the outside of the cement cartridge. The head of the ampoule is situated on the inside of the support socket. Rotating the ampoule holder about the support socket, the ampoule head is sheared off the ampoule body. The liquid can then be transferred from the ampoule into the cartridge through an opening in the cartridge wall. A mixing element is arranged at this site and can be used to mix a cement powder and the liquid from the ampoule.

WO 97/18031 A1 proposes a device, in which one ampoule is punctured on its bottom and the monomer liquid then can flow through a hollow mixing rod into the cement cartridge.

A system for mixing a medical cement in a vacuum is known from EP 1 031 333 A1. In this system, a motion of the mixing rod against a wedge-shaped device in the cartridge head moves the ampoule head obliquely against the ampoule axis, whereby the ampoule head is sheared off the ampoule body. The cement is mixed inside the mixing space by means of a mixing device.

A generic mixing device is known from DE 10 2007 061 696 B4, which describes a vacuum cementing system. The mixing device comprises a rotatable closure for closing-off a mixing cylinder. In the closed state, the components to be mixed can be mixed in the mixing cylinder using a mixing disc. Subsequently, the mixable material is dispensed from the vacuum cementing system through a dispensing tube. This is disadvantageous in that the rotatable closure needs to be taken off or lifted up to open the vacuum cementing system and produce a gas passage for sterilisation of the inside of the vacuum cementing system. Moreover, the vacuum is difficult to apply in the further course of the use of the vacuum cementing system since the evacuation must be effected through the cement powder.

The invention is based on the object to develop a device and a method making the handling of a vacuum cementing system simpler. Moreover, the sterilisation, the mixing of the components, and the application of a vacuum should be as easy as possible to perform.

Said object is met in that the closure is supported like in a bearing such that it can be rotated or shifted with respect to the cartridge head and in that a connection extends through the cartridge head or a cartridge wall into the inside of the cartridge and connects the inside of the cartridge to a container for a second component of the mixable material.

In this context, the invention can provide the connection to be a tube or a hose, whereby it is preferable to have a valve arranged between the connection and the container.

The invention can just as well provide the connection to be shiftable in the cartridge head along its axis of symmetry.

A refinement of the invention provides a filter and/or a sieve, in particular a pore filter, to be arranged between the at least one ventilation opening in the cartridge head and the inside of the cartridge that is filled with the first component.

The filter, sieve or pore filter serves to prevent ingress of the first component (for example a powder) into the region of the cartridge head.

Mixing devices according to the invention can also be characterised in that the mixing device comprises a dispensing tube or a fastening facility for a dispensing tube, whereby the dispensing tube can preferably be closed by means of a removable dispensing tube closure.

Moreover, the invention can provide the connection to comprise a lateral outlet in the region of the end of the connection that extends into the inside of the cartridge.

The invention can just as well provide the connection to comprise a predetermined breakage site between its outlet into the inside of the cartridge and the container, preferably in the region of the outlet.

Mixing devices according to the invention can also be characterised in that the closure is arranged between the cartridge head and the filter or sieve, preferably the pore filter, whereby at least one part, in particular at least one handle of the closure, preferably extends through the at least one ventilation opening in the cartridge head.

It can also be advantageous to have two ventilation openings be arranged in the cartridge head and be closable through two blades of the closure, whereby the ventilation openings and the blades are preferably designed as circle segments, and the closure to be rotatable.

A refinement of the invention provides the closure to have at least one handle, preferably two handles, arranged on it by means of which the closure can be rotated or shifted.

Moreover, the invention can provide a handle part to be connected or connectable to the dispensing tube or a mixing rod that extends through a centric opening in the cartridge head from the exterior to the inside of the cartridge and can be used to rotate the dispensing tube or the mixing rod inside the cartridge.

In this context, the invention can provide the dispensing tube closure to be a stopper on the inside of the dispensing tube that is connected to the handle part by means of which the stopper can be removed from the dispensing tube.

Mixing devices according to the invention can also be characterised in that at least one mixing vane is arranged on the dispensing tube or on the mixing rod and in that the dispensing tube or the mixing rod having the mixing vane or mixing vanes is supported like in a bearing in the cartridge such that it can be rotated.

Moreover, the invention can provide a vacuum connector to be arranged in the cartridge head or in a wall of the cartridge as a feed-through and to preferably comprise a valve closure for opening and closing the vacuum connector.

Another embodiment of the invention provides a feed plunger for dispensing the cartridge content to be arranged in the cartridge bottom.

It is particularly preferable for the first component to be a powder, in particular a cement powder for a PMMA bone cement, and the second component to be a liquid, in particular a monomer liquid.

The object of the invention is also met through a vacuum cementing system comprising a mixing device of this type.

Likewise, the object of the invention is met through a method for mixing a mixable material with a mixing device of this type or with a vacuum cementing system of this type.

In this context, the following procedural steps can be provided:

A) sterilising the inside and the content of the cartridge through the at least one open ventilation opening in the cartridge head, in particular through the use of ethylene oxide; B) closing the at least one ventilation opening in the cartridge head by means of rotating or shifting the closure with respect to the cartridge head or by means of rotating or shifting the cartridge head with respect to the closure;

C) evacuating gases from the inside of the cartridge;

D) feeding the second component of the container into the cartridge; and

E) mixing the first and the second component.

Sterilisation of the inside, and in particular of the content, of the cartridge shall be understood to include partial sterilisation and/or sterilisation of regions thereof.

Moreover, the invention can provide the mixture to be applied through a dispensing tube.

And lastly, the invention can provide, once the second component has been fed into the inside of the cartridge, the connection to the container to be severed and the non-centric passage for the connection to the container to be closed by means of rotating or shifting the closure with respect to the cartridge head or vice versa.

The invention is based on the surprising finding that a mixing device having a rotatable or shiftable closure for closing a ventilation opening can be designed to be very simple and cost-efficient. The functional principle of the mixing device in this context is so simple that it can be used easily at any time. Moreover, previous mixing devices can be retrofitted easily. In addition, a feed-through for the second component can be closed easily by means of a slightly modified closure mechanism without any need to have additional parts for this purpose. The closure system in this context is extraordinarily robust to interferences since it is easy to implement the shifting of a surface (a blade of the closure) over an opening.

The underlying closure principle is implemented, for example, in that a cover is present over a pore disc (above a pore filter) in the direction of a vacuum connector and comprises at least one ventilation opening as window. A rotatable or shiftable closure disc or a closure disc segment is arranged above this site and also comprises at least one ventilation opening. The ventilation opening or the ventilation openings then need to be rotatable or shiftable over the ventilation opening or ventilation openings of the lower disc such that a gas passage between the pore disc and the surroundings is made feasible. Rotating or shifting the closure disc must provide the ventilation opening or ventilation openings of the closure disc to not overlap with the ventilation opening or ventilation openings of the lower disc such that a gas exchange between the pore disc and the surroundings is possible only by means of a vacuum connector.

The rotatable closure comprises one or more ventilation opening(s) in the form of circle segments ("pieces of pie") or circle segment sections. The rotatable closure can cover or expose corresponding ventilation openings in the cartridge head.

Rotation of the closure can open and close the ventilation openings such that permeability for ethylene oxide is provided during the sterilisation while vacuum tightness can be attained during the application of cement by simply rotating the rotatable closure.

The rotatable closure can be rotated such that the ventilation openings in the cartridge head are closed to ethylene oxide sterilisation and vacuum can be drawn. After pulling out the tube, the rotatable closure can be rotated just a few degrees further such that the feed-through for the tube is also closed, once in the cartridge head and simultaneously in the pore disc. For this purpose, the underside of the rotatable closure has a planar surface that can cover the feed-through in the pore disc.

The functional principle of a mixing device according to the invention can be described as follows. Firstly, the rotatable closure in the cartridge head is rotated such that the ventilation openings for the ethylene oxide sterilisation are closed. Then, a vacuum is applied by means of the vacuum connector. Subsequently, a monomer reservoir container (containing the second component/a liquid monomer) is opened. The vacuum or gravity makes the monomer flow through the tube right into the cement powder (the first component). Once the monomer is transferred into the cement powder, the tube with the monomer reservoir container are pulled out of the inside of the cartridge. Then, the rotatable closure is rotated a few degrees further such that the feed-throughs for the tube in the cartridge head and in the pore disc are also sealed in such manner that the mixing can proceed in a vacuum subsequently. Once the mixing process is completed, the stirring rod/mixing rod is pulled onto the mixing head and the closure in the hollow stirring rod/mixing rod is pulled out. This exposes the dispensing tube and allows the cement to be squeezed out through the dispensing tube.

Figure 2:
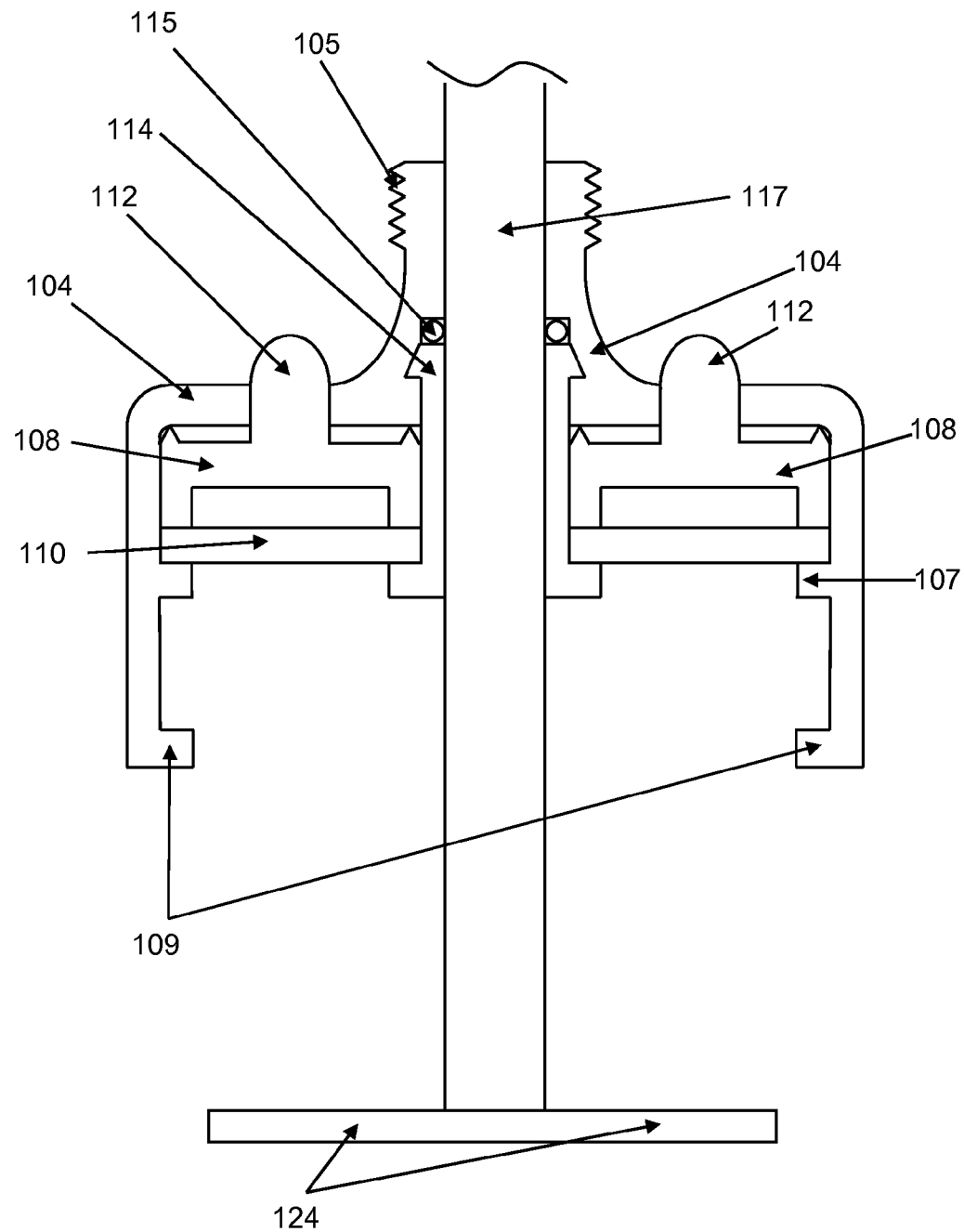
Figure 3:
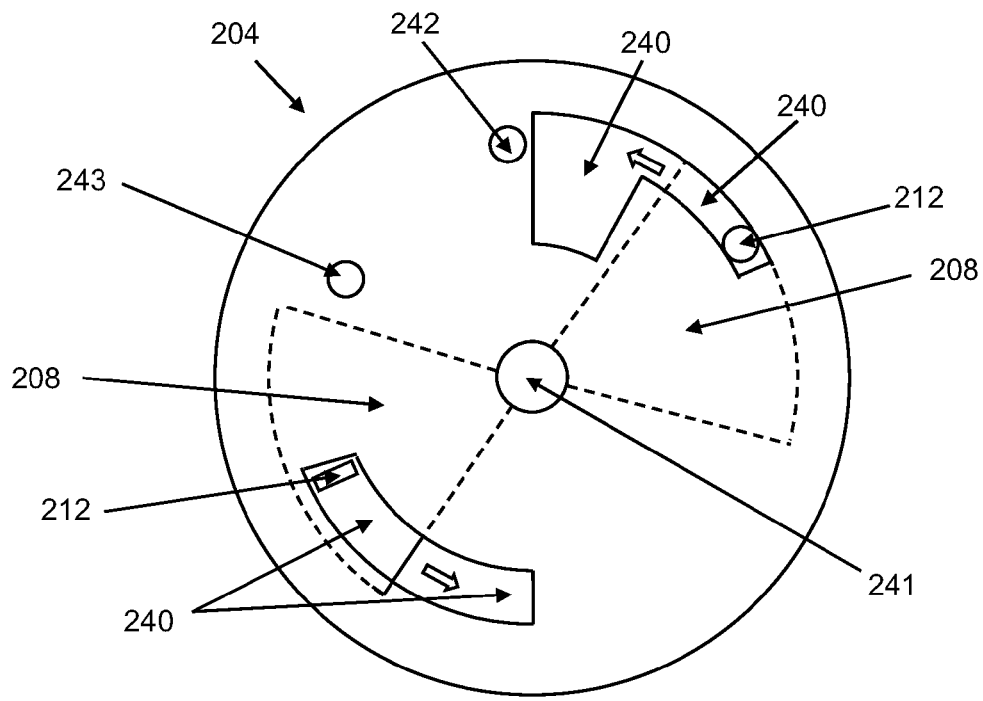
Figure 4:
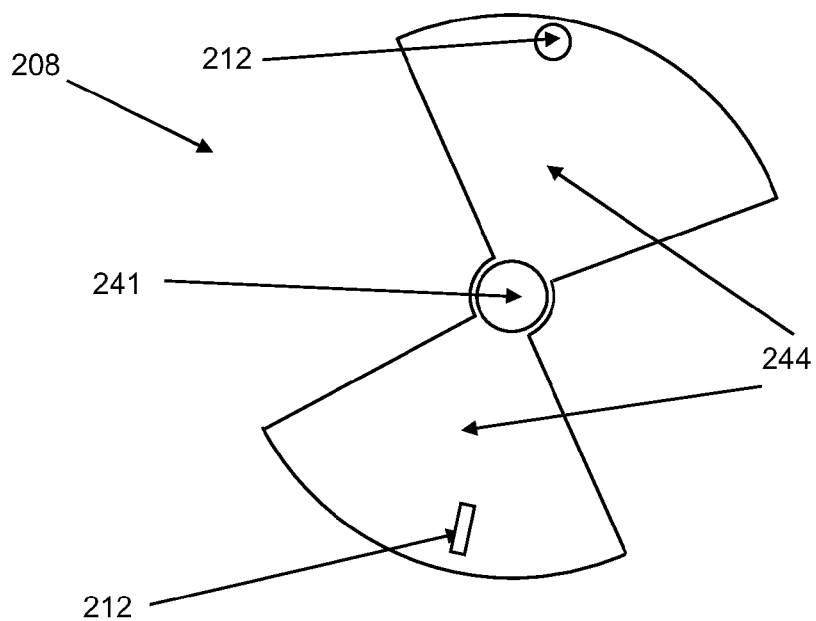
Figure 5:
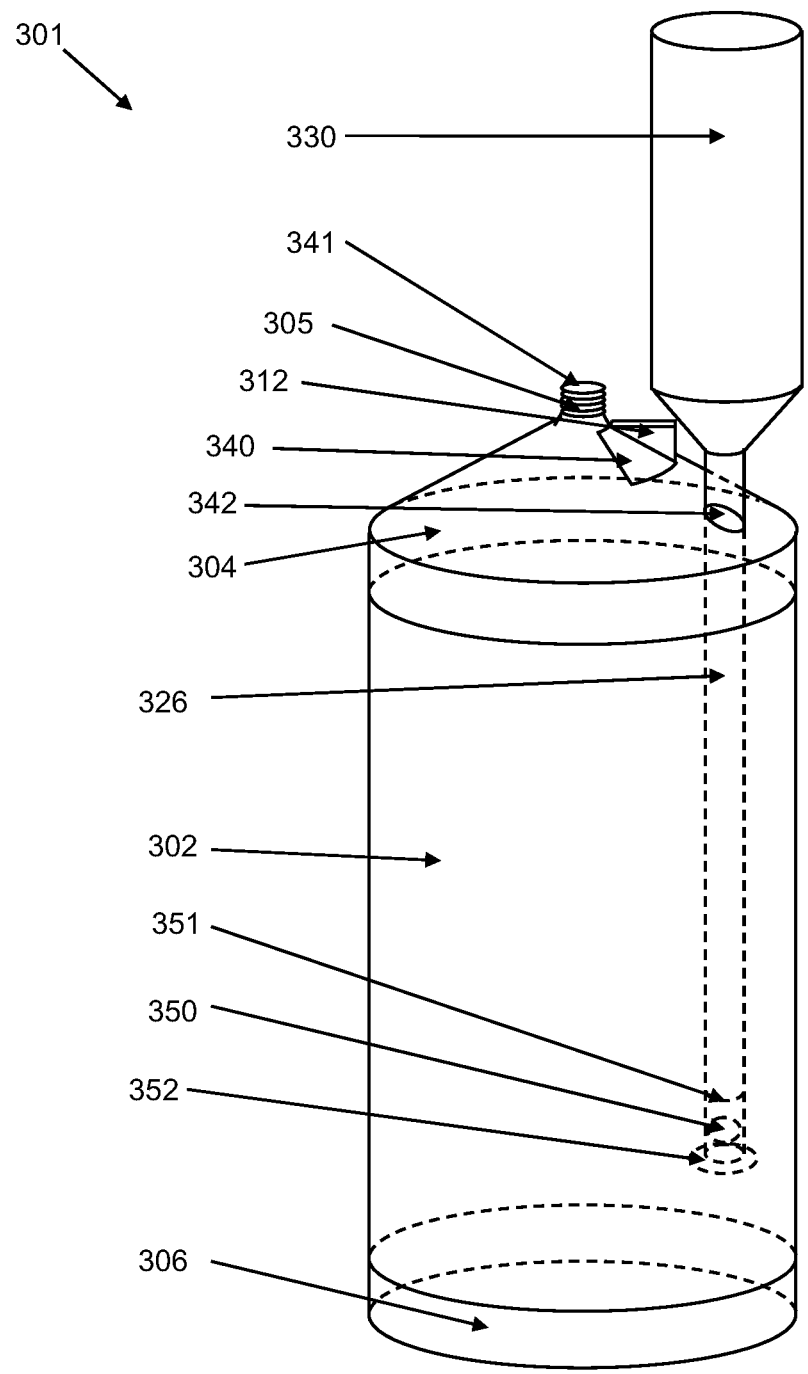
Figure 6A:
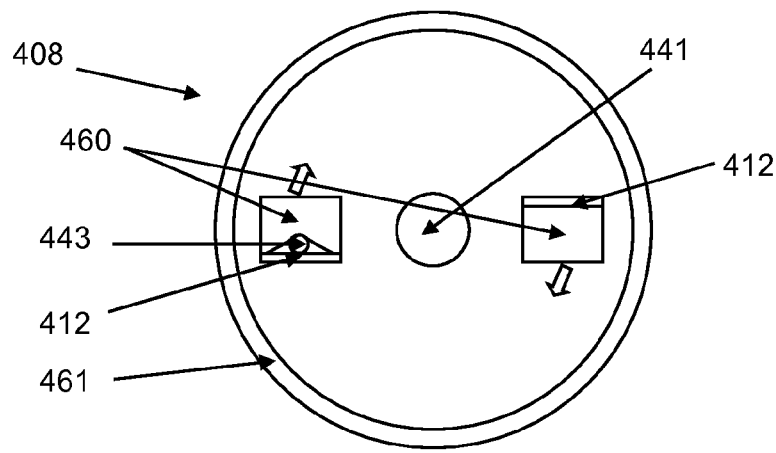
Figure 6B:
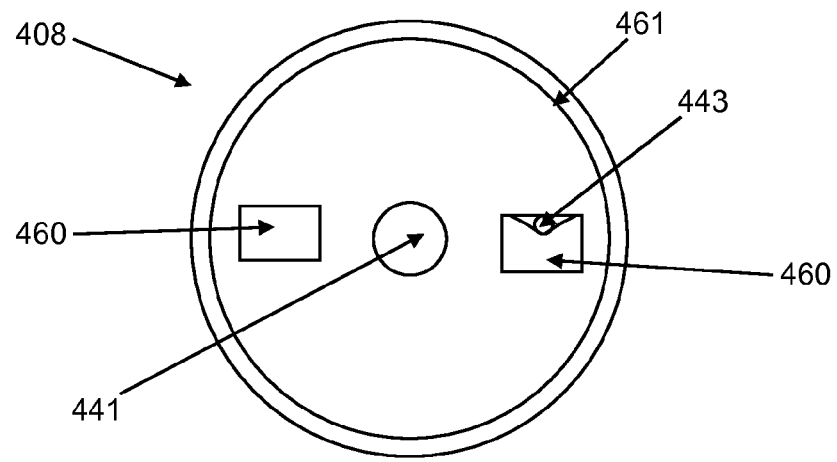
Figure 6C:
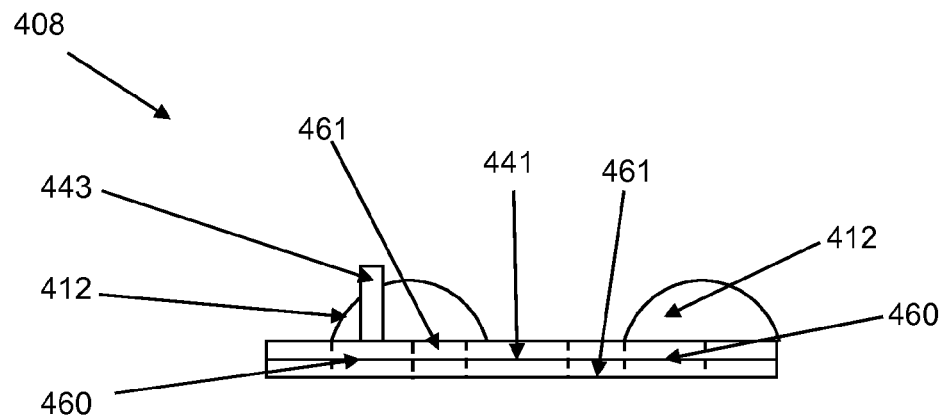
Figure 7:
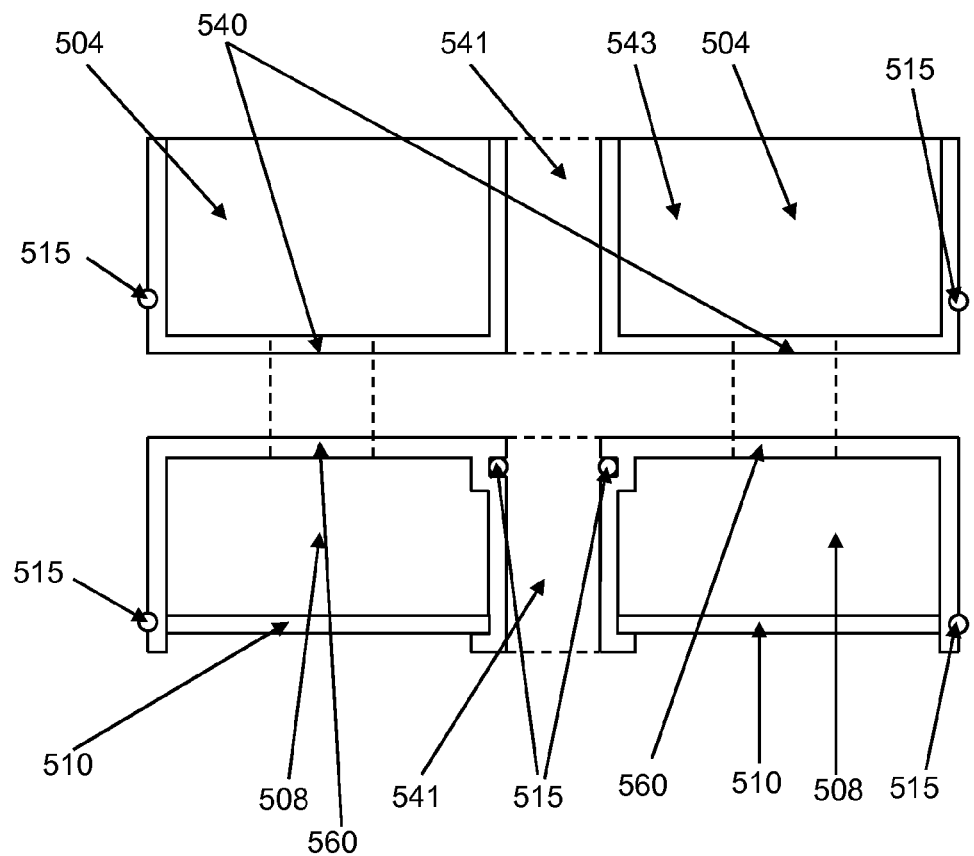
Figure 8A:
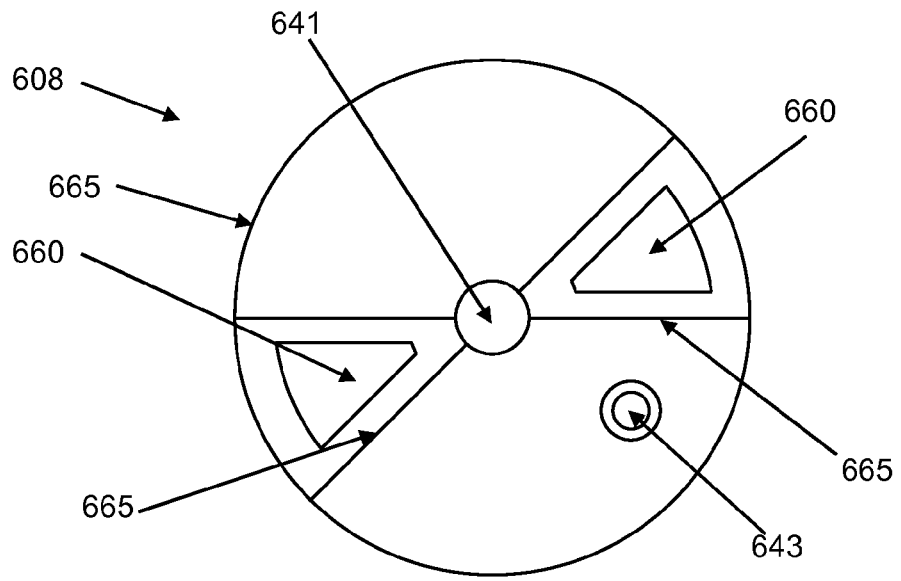

In the following, exemplary embodiments of the invention are illustrated through eight schematic drawings. In the figures:

FIG. 1: shows a schematic cross-sectional view in longitudinal direction of a mixing device according to the invention;

FIG. 2: shows a schematic cross-sectional view in longitudinal direction of a part of a mixing device according to the invention;

FIG. 3: shows a schematic top view onto a mixing device according to the invention;

FIG. 4: shows a schematic top view onto a closure of a mixing device according to the invention;

FIG. 5: shows a perspective view of a mixing device according to the invention;

FIG. 6A: shows a schematic view from above of a closure for a mixing device according to the invention;

FIG. 6B: shows a schematic view from below of a closure for a mixing device according to the invention;

FIG. 6C: shows a schematic view from the side of a closure for a mixing device according to the invention;

FIG. 7: shows a schematic cross-sectional view of an insert in the cartridge head of a mixing device according to the invention; and FIG. 8A: shows a schematic top view, of the upper part, onto inserts for mixing devices according to the invention;

FIG. 8: shows a schematic top view, of the lower part, onto inserts for mixing devices according to the invention.

All mixing devices according to the invention, parts of the mixing devices, and vacuum cementing systems according to the invention described above are suitable for implementing methods according to the invention.

FIG. 1 shows a schematic cross-sectional view of a mixing device according to the invention. The mixing device (1) comprises a cartridge (2) having a cartridge head (4) that is connected to the cartridge body by means of fastening means (6) in the form of a thread. The bottom side of the cartridge (2) is closed through a feed plunger (6) that is arranged such as to be mobile in the direction of the cartridge head (4). Below the cartridge head (4) are arranged a closure (8), supported like in a bearing such as to be rotatable, and, below it, a pore filter (10) between the cartridge head (4) and the inside of the cartridge (2). The purpose of the pore filter (10) is to keep a powder stored on the inside of the cartridge (2) from reaching the closure (8) whereas gases can pass the pore filter (10) easily.

The closure (8) comprises two handles (12) that extend through two ventilation openings in the cartridge head (4). The ventilation openings in the cartridge head (4) are larger than the handles (12) of the closure (8). Rotating the closure (8) allows the ventilation openings in the cartridge head (4) to be opened and closed.

Centric openings are provided in the centre of the cartridge head (4), of the closure (8), and of the pore filter (10) and have a guide sleeve (14) arranged in them which concurrently serves as bracket and can comprise a seal (not shown). A feed-through for a dispensing tube (16) is provided on the inside of the guide sleeve (14), whereby the dispensing tube (16) extends through the centric openings of the cartridge head (4), of the closure (8), and of the pore filter (10) into the inside of the cartridge (2). The dispensing tube (16) is clogged in the direction of the feed plunger (6) by means of a dispensing tube closure (18). The dispensing tube closure (18) is connected to a handle part (22) through a rod (20). The handle part (22) closes the dispensing tube (16) at the tip outside of the cartridge (2). The handle part (22) is attached on the tip of the dispensing tube (16) in such manner that rotating the handle part (22) also rotates the dispensing tube (16) in the cartridge (2). Two mixing vanes (24), which are connected to the dispensing tube (16) on the inside of the cartridge (2), then also rotate along with the dispensing tube (16). Loosening the fastening of the handle part (22) and pulling out the handle part (22) with the rod (20) also removes the dispensing tube closure (18) from the dispensing tube (16) and the vacuum cementing system formed by means of the mixing device (1) is then ready for application of a cement from the inside of the cartridge (2).

Especially if the mixing device (1) or parts of the mixing device (1), preferably of the cartridge (2) and the cartridge head (4), has/have a cylindrical design, both the dispensing tube (16) and the closure (8) can be rotated about the axis of symmetry.

A tube (26) or a hose extends through a non-centric feed-through through the cartridge head (4), the closure (8), and the pore filter (10) into the inside of the cartridge (2), all the way into the first component, for example the cement powder. The non-centric feed-through for the tube (26) in the closure (8) extends along an arc of a circle such that the closure (8) can be transitioned from the closed to the open position of the ventilation openings in the cartridge head (4), and vice versa, without the tube (26) impeding the motion of the closure (8).

The open end of the tube (26) on the inside of the cartridge (2) is covered by means of a filter (28) that allows only gaseous or liquid substances to pass, and/or a sieve is attached at this site. A container (30) is arranged on the other end of the tube (26) and has a liquid situated in it which, together with the powder in the cartridge (2), forms a cement. An operable valve (32) is arranged between the tube (26) and the container (30). Said valve (32) is closed initially. The tube (26) can be arranged in the non-centric feed-throughs in the cartridge head (4), the closure (8), and the pore filter (10) such that it is mobile along its axis of symmetry.

The mixing device (1) is in the open state initially, i.e. the ventilation openings in the cartridge head (4) are initially not covered through the closure (8). In this state, the mixing device (1) is sterilised first, for example through supplying ethylene oxide gas. The ethylene oxide enters through the ventilation openings in the cartridge head (4) and the pore filter (10) into the inside of the cartridge (2) such that complete sterilisation is made feasible.

Next, the ventilation openings in the cartridge head (4) are closed manually through rotating the closure (8) by the handles (12). Subsequently, the inside of the cartridge (2) is evacuated using a vacuum connector (not shown). Then, the valve (32) is opened such that the liquid content of the container (30) flows through the tube (26) and the filter (28) into the inside of the cartridge (2). The tube (26) is then pulled out completely or just a bit from the inside of the cartridge (2). Subsequently, the closure (8) is rotated further such that the non-centric feed-through for the tube (26) in the cartridge head (4) and in the pore filter (10) is closed. In the process, the tube (26) can just as well be broken off or cut off through the rotation of the closure (8). In another intermediate step, the inside of the cartridge (2) can be evacuated again.

Rotating the handle part (22) also rotates the dispensing tube (16) with the mixing vanes (24) and thus mixes the second component from the container (30) with the cement powder as the first component in the cartridge (2). This generates the mixable material, which, in this case, is the cement. The dispensing tube (16) is then pulled out up to the guide sleeve (14) from the inside of the cartridge (2) or pushed out through applying a pressure on the feed plunger (6). Removing the handle part (22) with the dispensing tube closure (18) opens the mixing device (1). Subsequently, the finished cement can be applied through the dispensing tube (16) using the feed plunger (6).

FIG. 2 shows a cross-sectional view of the schematic design of parts of an alternative mixing device. Two closures (108) that are supported like in a bearing such as to be shiftable and a filter (110) in the form of a washer are arranged in the bracket (107) in a cartridge head (104) that is shown in the figure and comprises a thread (105) for connecting a dispensing tube, two ventilation openings, and a centric opening as well as a bracket (107). One handle (112) each of the closures (108) extends through the ventilation openings. The ventilation openings in the cartridge head (104) can be closed and opened through shifting the closures (108). The lower end of the cartridge head (104) has fastening means in the form of pegs (109) arranged on it that enable fastening of the cartridge head (104) to a cartridge body (not shown).

A guide sleeve (114) and a sealing ring (115) are arranged in the centric opening. The guide sleeve (114) serves for positioning the closures (108), the filter (110), and the sealing ring (115) as well as the guide of a mixing rod (117) that extends through the centric opening of the cartridge head (104). A snap-in mechanism for fastening the guide sleeve (114) on the cartridge head (104) is provided at the upper end of the guide sleeve (114). The purpose of the sealing ring (115) is to close the centric opening together with the mixing rod (117) in gas-tight manner. Two mixing vanes (124) are plugged onto the mixing rod (117). The mixing rod (117) can be pulled out through the centric opening upon which the mixing vanes (124) fall off or fold away. Subsequently, a dispensing tube can be fastened to the external thread (105) of the cartridge head (104). The dispensing tube (not shown) has an internal thread for this purpose.

The mixing rod (117) is supported like in a bearing such that it can rotate such that rotating the mixing rod (117) also rotates the mixing vanes (124) and such that the parts shown form a mixing attachment of the type of a mixer for a cartridge (not shown).

A pore disc can be used as filter (110). Instead of two shiftable closures (108), it is feasible to use, as closure (108), a single perforated ring that is supported like in a bearing such that it can rotate. The perforations in the ring-shaped closure (108) overlap with the ventilation openings in the cartridge head (104) when the closure (108) is in the open position. This is advantageous in that just one closure (108) needs to be moved to close the ventilation openings of the mixing system.

Fins or support rings shaped as fins are arranged at the top of the shiftable closures (108) or of the rotatable closure (108) and establish contact to the upper side of the cartridge head (104). The spacing thus established can ensure that a vacuum connector (not shown) stays open at all times regardless of the position of the closure (108).

Connecting said parts and/or said insert to a cartridge filled with a first component and connected to an additional container containing a second component results in a mixing device according to the invention.

FIG. 3 shows a schematic top view onto a mixing device according to the invention. Five openings are provided in a circular cartridge head (204) and can be closed partly by means of a closure (208) (identified through dotted lines in FIG. 3) that is arranged below the cartridge head (204). Two of said openings are closable ventilation openings (240) in the form of circle segment sections ("cut off/nibbled pieces of pie"). The non-closable centric opening (241) serves for feed-through of a mixing rod and/or a dispensing tube into the inside of a cartridge, in which a first powder-shaped component for production of the mixable material is situated. A closable, non-centric feed-through (242) serves for feed-through of a tube that is connected to a container containing a liquid second component for production of the mixable material. The final opening is a non-closable vacuum connector (243) through which the inside of the cartridge can be evacuated. A one-way valve (not shown) can be arranged in the vacuum connector (243).

Supported like in a bearing such that it can rotate about the centric opening (241) and also shown schematically in FIG. 4, closure (208) comprises two blades (244) in the form of circle segments ("pieces of pie") that can cover the ventilation openings (240) and the non-centric feed-through (242) depending on the position of the closure (208).

If the mixing device is in an open state as the one shown in FIG. 3, the ventilation openings (240) and the non-centric feed-through (242) are not covered through the closure (208). The inside of the cartridge can be sterilised using a gas through the ventilation openings (240). Subsequently, the closure (208) is rotated in the direction of the open arrows such that the ventilation openings (240) are closed. The closure (208) cannot be rotated further since a tube is plugged into the non-centric feed-through (242).

Subsequently, the mixing device is evacuated through the vacuum connector (243). A liquid second component is guided and/or aspirated through the tube in the non-centric feed-through (242) into the inside of the cartridge and mixed therein with the first powder-shaped component. For the purpose of mixing, a mixing rod is guided through the centric opening (241) and has one or more mixing vanes arranged on its end such that a rotation of the mixing rod is associated with the two components being mixed.

Subsequently, the tube is pulled out of the non-centric feed-through (242). Subsequently, continuing the rotation of the closure (208) can also lead to the non-centric feed-through (242) being covered through the closure (208). If the mixing rod is hollow or has been taken out, the finished mixable material can be expelled from the cartridge through the centric opening (241).

It may be sensible after each intermediate step, in which one of the openings (240, 242) is being closed, to evacuate the inside of the cartridge using the vacuum connector (243).

FIG. 5 shows a schematic perspective view of a mixing device (301) according to the invention. The mixing device (301) comprises a cartridge (302) that is covered through a cartridge head (304) and closed in pressure-tight manner. The cartridge head (304) has a ventilation opening (340) situated in it that can be closed through a closure (not shown) that is supported like in a bearing such as to be rotatable or shiftable and is arranged below the cartridge head (304). The closure can be rotated or shifted through the use of a handle (312) by means of which the ventilation opening (340) can be opened and closed. The handle (312) projects through the ventilation opening (340) outward.

A centric opening (341) that is formed through a tube that has a thread (305) arranged on its outside is situated in the middle of the cartridge head (304). A tube (326) connected to a container (330) extends through a non-centric feed-through (342). The tube (326) merges into an outlet (350) that is arranged on the side of the tube wall on the inside of the cartridge (302). The bottom-side end of the tube (326) is closed. The cartridge (302) contains a first component, whereas the container (330) contains a second component. The second component can be guided through the tube (326) to the first component. A predetermined breakage site (351) and a limit stop (352) in the form of a washer on the tube (326) are arranged in the region of the outlet (350). Accordingly, the tube (326) can be pulled through the non-centric feed-through (342) only to the limit stop (352). The same is then closed through the lateral positioning of the outlet (350). The tube (326) can then be broken off easily at the predetermined breakage site (351) and the mixing device (301) remains closed in tight manner, whereas the empty container (330) can be removed.

A mixing rod (not shown) can be guided into the inside of the cartridge (302) through the centric opening (341) to mix the two components on the inside of the cartridge (302). A dispensing tube (not shown) can be screwed onto the thread (305).

FIG. 6 shows a schematic view of a closure (408) for a mixing device according to the invention that is provided as a rotatable, perforated ring. In this context, FIG. 6A shows a top view (from the direction of the cartridge head), FIG. 6B shows a view from below (from the direction of the cartridge bottom), and FIG. 6C shows a side view.

The ring-shaped closure (408) has a centric opening (441) in the middle. The edge of the closure (408) has a support ring (461) on the upper and the lower side situated on it. The closure (408) further comprises two ventilation openings (460) that can be used to set a patent ventilation opening to the inside of a mixing device according to the invention when the ventilation openings (460) overlap with corresponding ventilation openings in a cartridge head (not shown) of a mixing device according to the invention.

The position of the closure (408) can be set through rotating the closure. For this purpose, two handles (412) are provided on the closure (408) in the region of the ventilation openings (460). A vacuum connector (443) is arranged on one of the handles (412).

A closure (408) of this type can be arranged either below or above a cartridge head and thus contribute to a mixing device according to the invention.

FIG. 7 shows a schematic cross-sectional view of a cartridge head (504) having a closure (508) and their concerted action for formation of a mixing device according to the invention. Both the cartridge head (504) and the closure (508) are designed to be ring-shaped and comprise seals (515) at their external walls that seal the mixing device in a vacuum-tight and pressure-tight manner when the cartridge head (504) and the closure (508) are inserted into a hollow cylinder-shaped cartridge (not shown).

Another seal (515) is provided on the inside of the closure (508) for sealing the mixing device when a mixing rod or a dispensing tube is inserted into a centric opening (541) of the closure (508) and of the cartridge head (504).

A pore filter (510) is arranged in a bracket of the closure (508) and completely closes the closure (508) on its bottom-side. Two ventilation openings (560) are provided on the upper side of the closure (508). Said ventilation openings (560) of the closure (508) correspond to two ventilation openings (540) of the cartridge head (504). Moreover, a vacuum connector (543) is provided in the cartridge head (504). The vacuum connector (543) can have a valve arranged in it that permits exclusively a flow out of the mixing device (upwards in FIG. 7).

The closure (508) is arranged such as to be rotatable with respect to the cartridge head (504). When the ventilation openings (540) of the cartridge head (504) overlap with the ventilation openings (560) of the closure (508), a patent ventilation opening is generated. Rotating the closure (508) or the cartridge head (504) closes said ventilation opening.

Figure 8B:
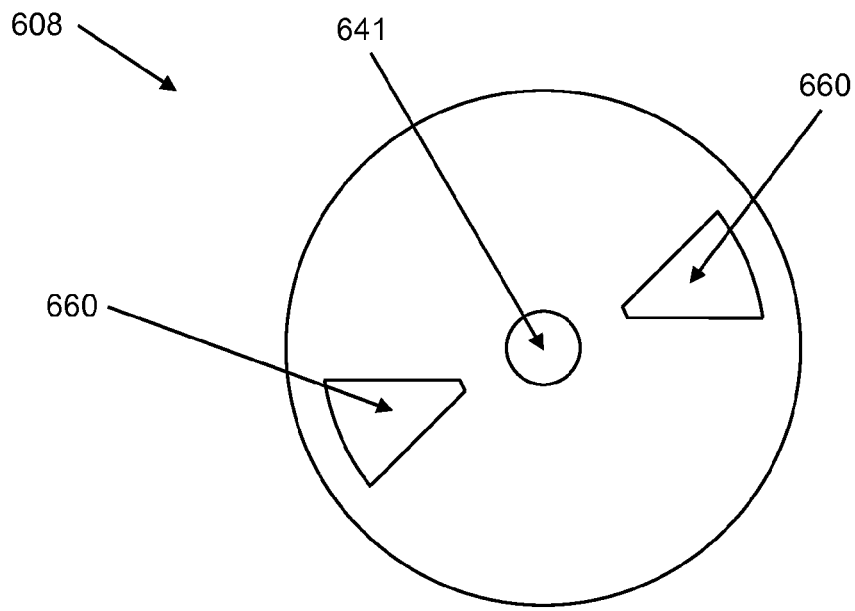

FIGS. 8A and 8B show schematic views of a closure (608) according to the invention for a mixing device according to the invention from above (FIG. 8A) and from below (FIG. 8B). A centric opening (641) is provided in the centre of the circular closure (608). Moreover, ventilation openings (660) are provided in the form of circle segments in the closure (608). In addition, a vacuum connector (643) is provided in the upper side of the closure (608).

Fins (665) are arranged on the upper side of the closure (608) and are used to keep a spacing from a cartridge head (not shown) that is arranged above the closure (608). The fins (665) are arranged circumferentially on the edge of the closure (608) and around the ventilation openings (660) and the centric opening (641).

The features of the invention disclosed in the preceding description and in the claims, figures, and exemplary embodiments, can be essential for the implementation of the various embodiments of the invention both alone and in any combination.

LIST OF REFERENCE NUMBERS

1, 301 Mixing device
2, 302 Cartridge
4, 104, 204, 304, 504 Cartridge head
105, 305 Thread
6, 306 Feed plunger
107 Bracket
8, 108, 208, 408, 508, 608 Closure
109 Pegs
10, 110, 510 Pore filter
12, 112, 212, 312, 412 Handle on the closure
14, 114 Guide sleeve
115, 515 Seal
16 Dispensing tube
117 Mixing rod
18 Dispensing tube closure
20 Rod
22 Handle part
24, 124 Mixing vane
26, 326 Tube
28 Filter
30, 330 Container
32 Valve
240, 340, 540 Ventilation opening
241, 341, 441, 541, 641 Centric opening
242 Non-centric feed-through
243, 443, 543, 643 Vacuum connector
244 Blade of the closure
350 Outlet
351 Predetermined breakage site
352 Limit stop
460, 560, 660 Ventilation openings in the closure
461 Support ring
665 Fin
Mixing device for prepack vacuum cementing system

The invention claimed is:

1. A mixing device for mixing a mixable material and adapted for applying vacuum, the mixing device comprising at least one cartridge and one closure, whereby the at least one cartridge contains a first powder component of the mixable material and comprises a cartridge head, in which at least one ventilation opening is arranged and the closure is arranged at the cartridge head in such manner that the at least one ventilation opening in the cartridge head can be closed and opened by means of the closure, wherein the closure is supported such that it is rotatable or shiftable with respect to the cartridge head and that when the closure is closed, vacuum can be drawn in the cartridge head and in that a connection extends through the cartridge head or a cartridge wall into the inside of the cartridge and connects the inside of the cartridge to a closed container for a second liquid component of the mixable material and further wherein a filter and/or a sieve is arranged between the at least one ventilation opening in the cartridge head and the inside of the cartridge that is filled with the first component and the closure is arranged between the cartridge head and the filter or sieve, whereby at least one part of the closure extends through the cartridge head.

2. The mixing device according to claim 1, wherein the connection is a tube or a hose, whereby a valve is arranged between the connection and the container.

3. The mixing device according to claim 1, wherein the connection is shiftable in the cartridge head along an axis of symmetry of the connection.

4. The mixing device according to claim 1, further comprising: a pore filter arranged between the at least one ventilation opening in the cartridge head and the inside of the cartridge that is fillable with the first component.

5. The mixing device according to claim 1, further comprising: a dispensing tube or a fastening facility for a dispensing tube, whereby the dispensing tube is closable by means of a removable dispensing tube closure.

6. The mixing device according to claim 1, wherein the connection comprises a lateral outlet in a region of a end of the connection that extends into the inside of the cartridge.

7. The mixing device according to claim 1, wherein the connection comprises a predetermined breakage site between a lateral outlet into the inside of the cartridge and the container, in the region of the lateral outlet.

8. A mixing device according to claim 4, wherein the closure is arranged between the cartridge head and the pore filter, whereby at least one handle of the closure extends through the at least one ventilation opening in the cartridge head.

9. The mixing device according to claim 1, further comprising: two ventilation openings arranged in the cartridge head and closable through two blades of the closure, whereby the ventilation openings and the blades are designed as circle segments, and the closure is rotatable.

10. The mixing device according to claim 1, wherein the closure has at least one handle arranged thereon by means of which the closure can be rotated or shifted.

11. The mixing device according to claim 5, further comprising: a handle part connected or connectable to the dispensing tube or a mixing rod that extends through a centric opening in the cartridge head from an exterior to the inside of the cartridge and is usable to rotate the dispensing tube or the mixing rod inside the cartridge.

12. The mixing device according to claim 11, wherein the dispensing tube closure is a stopper on the inside of the dispensing tube that is connected to the handle part by means of which the stopper is removable from the dispensing tube.

13. The mixing device according to claim 4, further comprising: at least one mixing vane arranged on a dispensing tube or on the mixing rod and in that the dispensing tube or the mixing rod having the at least one mixing vane is supported in the cartridge such that it can be rotated.

14. The mixing device according to claim 1, further comprising: a vacuum connector arranged in the cartridge head or in a wall of the cartridge as a feed-through and comprises a valve closure for opening and closing the vacuum connector.

15. A mixing device according to claim 1, further comprising: a feed plunger for dispensing the cartridge content arranged in the cartridge bottom.

16. The mixing device according to claim 1, wherein the first component is a cement powder for a PMMA bone cement, and the second component is a monomer liquid.

17. A vacuum cementing system comprising the mixing device according to claim 1.

18. A method for mixing a mixable material with the mixing device according to claim 1, the method comprising:

A) sterilizing the inside and the content of the cartridge through the at least one open ventilation opening in the cartridge head;
B) closing the at least one ventilation opening in the cartridge head by means of rotating or shifting the closure with respect to the cartridge head or by means of rotating or shifting the cartridge head with respect to the closure;
C) evacuating gases from the inside of the cartridge;
D) feeding the second component of the container into the cartridge; and
E) mixing the first and the second component to form a mixture.

19. The method according to claim 18, further comprising: applying the mixture through a dispensing tube.

20. The method according to claim 18, wherein, once the second component has been fed into the inside of the cartridge, the connection to the container is severed and the non-centric passage for the connection to the container is closed by means of rotating or shifting (i) the closure with respect to the cartridge head or (ii) the cartridge head with respect to the closure.

\* \* \* \* \*